United States Patent [19]

Sun

[11] Patent Number: 5,333,165

[45] Date of Patent: Jul. 26, 1994

[54] METHOD AND APPARATUS FOR THREE-DIMENSIONAL VIDEO SIGNALS

[75] Inventor: Ying Sun, Wakefield, R.I.

[73] Assignee: John K. Grady, Harvard, Mass.

[21] Appl. No.: 842,650

[22] Filed: Feb. 27, 1992

[51] Int. Cl.$^5$ .......................................... G01N 23/083
[52] U.S. Cl. ...................................... 378/10; 378/901; 364/413.15; 364/413.19
[58] Field of Search ...................... 364/413.15, 413.19, 364/413.22; 378/3, 10, 901

[56] References Cited

U.S. PATENT DOCUMENTS

| 4,002,913 | 1/1977 | LeMay | 250/44 ST |
| 4,037,585 | 7/1977 | Gildenberg | 128/2 A |
| 4,422,146 | 12/1983 | Yamaguchi et al. | 364/414 |

OTHER PUBLICATIONS

Soumekh, Mehvad; "Binary Image Reconstruciton from Four Projections" Apr. 1988; pp. 1280–1283; International Conference on Acoustics, Speech, and Signal Processing, New York.

Primary Examiner—Paul M. Dzierzynski
Assistant Examiner—David V. Bruce
Attorney, Agent, or Firm—James H. Grover

[57] ABSTRACT

A method and apparatus for processing three-dimensional video signals representing a solid subject comprises, radiating the subject, receiving radiation from the subject with receptors on three axes intersecting the subject to produce three planar images of the subject volume normal to the three respective radiation axes. The picture elements of the three planar images are converted into three corresponding sets of planar video pixel signals which are converted into voxels and written at the three radiation axes into superimposition in a three dimensional storage matrix such that coincidence of three pixels in the three respective images stores a single voxel representative of the superposition of the three pixels. The voxels in the matrix can then be addressed by a view selector at an angle other than the three original radiation axes to read the selected two dimensional view out of the matrix to a display or recorder.

25 Claims, 3 Drawing Sheets

METHOD AND APPARATUS FOR THREE-DIMENSIONAL VIDEO SIGNALS

BACKGROUND OF THE INVENTION

In photographic and X-ray examination of subjects it is often advantageous to produce a three-dimensional image of the subject which can then be electronically viewed from various selected angles to reconstruct one or more desired new two-dimensional views of the subject other than the immediate views dictated by the exposure apparatus. This has been possible with well known computer assisted tomography and magnetic resonance imaging systems which expose multiple two-dimensional video images, and then extract the video information from many two-dimensional images by computer processing. Computer assisted tomography requires several minutes to acquire the many exposures around the subject's heart, too long a time to obtain sharp images of the pulsing heart and blood vessels. Magnetic resonance imaging lacks the resolution of X-radiology, or obtains resolution at the expense of long exposure periods. Other systems employing fast rotating X-ray tubes are very slow because they require that the exposures be gated by cardiographic pulses; and their cost is prohibitive for routine clinical use. Other methods involving reconstruction of views around a common rotation axis are impractical because of the computational complexity and time.

It is the object of the present invention to provide a method and apparatus for producing three-dimensional video signals of a three-dimensional subject, such as tree-like group of branched blood vessels, from which signals a desired two-dimensional view at any selected view angle may be reconstructed in real time (in seconds), with resolution as clear as conventional direct exposures, and using uncomplicated, stationary X-ray tube exposures. A further object is to exclude artifacts from such reconstructions.

SUMMARY OF THE INVENTION

In one aspect of the invention a method of processing three-dimensional video signals representing a solid subject comprises radiating the subject; receiving radiation from the subject on three axes intersecting the subject to produce three planar images of the subject volume normal to the three respective radiation axes; converting the picture elements of the three planar images into three corresponding sets of planar video pixel signals; writing the three planar signal sets at the three radiation axes into superimposition in a three dimensional storage matrix such that coincidence of three pixels in the three respective images stores a single voxel representative of the superposition of the three pixels; addressing voxels on a selected view angle toward the three dimensional matrix other than the angles of the three radiation axes; reading the addressed voxels of the selected view angle out of the matrix; and displaying (including recording) a two-dimensional image of the voxels read out at the selected view angle. Voxels are small elements of a volume, just as pixels are basic picture elements. The matrix need not be stereoscopically spaced, but corresponds electrically to a geometric solid volume such as a cube.

The method is particularly applicable to a tree-like vascular structure of little volume, and includes comparison of the gray scale signals representing the three planar images with voxels in the matrix to exclude artifacts.

In another aspect the invention comprises electrical apparatus for processing three dimensional video signals representing a solid subject comprising three receptors of radiation on three different image axes intersecting the subject at three different angles for converting the radiation to three corresponding two-dimensional video images respectively represented by three sets of pixels; a voxel generator coupled to the three receptors for producing one three-dimensional set of voxels at the three-dimensional intercept of pixels projected from the three two-dimensional pixel sets; a three-dimensional voxel matrix for storing the voxels; adjustable means connected to the voxel matrix for selecting a viewing axis scanning the three-dimensional matrix at an angle other than the radiation axis angles, and addressing and reading out voxels within the selected view; and means coupled to the matrix for displaying the addressed and read out voxels of the selected three-dimensional view in a single two-dimensional image.

DESCRIPTION

Figure 1:
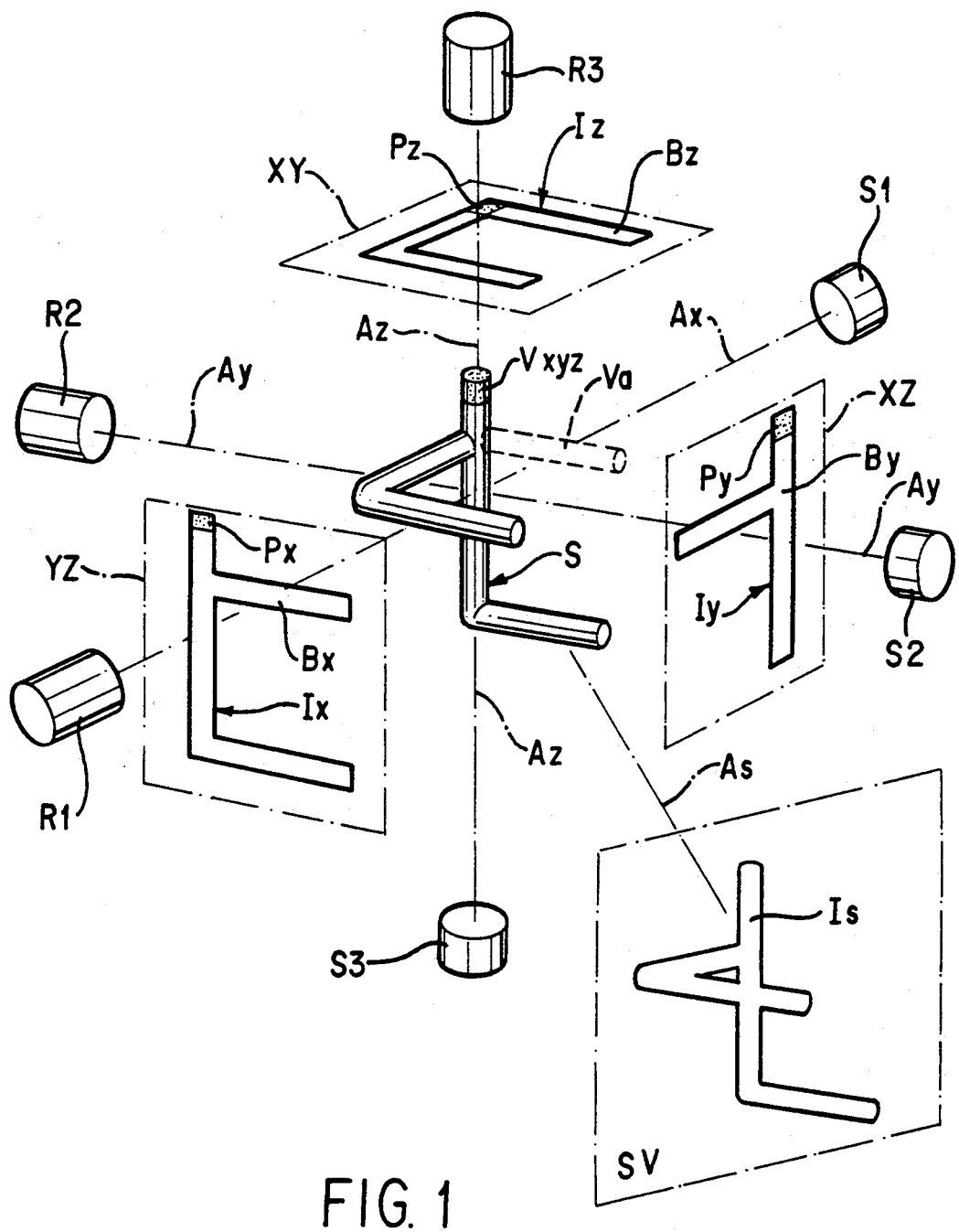
FIG. 1 is a diagrammatic view illustrating the method of processing three-dimensional video signals of a solid subject.

FIG. 1 shows schematically the first step of forming a three dimensional image by radiating a solid, i.e. three-dimensional, subject S by three radiation sources S1, S2, S3 along three radiation axes Ax, Ay, Az directed through the subject in the case of X-ray examination and onto three corresponding radiation receptors Rx, Ry, Rz. For photographic examination ambient light replaces the three sources and the receptors receive reflected light. In either case the three receptors respectively receive different planar, i.e. two-dimensional, images of the subject S corresponding to the views of the subject on the three axes substantially simultaneously. As shown, the three axes are mutually orthogonal, but may deviate somewhat from that relation, between solid angles of 45 to ninety degrees. With orthogonal axes the three, two-dimensional planar images received by the receptors correspond to image Ix in plane YZ, image Iy in plane XZ and image Iz in plane XY. In practice the three images are received by video camera, X-ray image intensifiers, or like radiation receeptors which convert the images into three corresponding sets of planar video signals composed of a series of electrical picture signal elements or pixels with black to white amplitudes distributed on a continuous gray scale. Thus the planar images Ix, Iy and Iz are composed of many pixels such as elements Px, Py and Pz.

For the purpose of explanation the cube bounded by the image planes XY, XZ, YZ my be conceived as a three-dimensional matrix for storing the three planar video signals as voxels or three-dimensional volume elements of the original solid subject S.

According to the method aspect of the invention, after the gray scale signals are converted to binary, on-off signals, in effect, the three planar video signals are electrically projected back along the original radiation axes into the storage matrix represented by the cube using a computer and appropriate algorithm to write into the matrix. Where three back pixels coincide in the theoretical three-dimensional storage space of the matrix a single voxel is stored. When all the coincident pixels are stored as voxels in the matrix it contains a three-dimensional record of the original subject S. The three-dimensional electrical record in the matrix can then be scanned along a selected axis As at any desired view angle, other than one of the orthogonal radiation axes, by addressing voxels around an axis at the selected view angle, and reading the addressed voxels out of the matrix as a two-dimensional image Is or the subject in a new viewing plane Sv at the new view angle for display or recording photographically or by computer printout. Against the possibility that artifacts might be introduced into the three-dimensional record in the matrix, the three gray video signals produced by the receptors are interatively compared by a filter with corresponding voxels in the matrix so as to exclude storage in the matrix of an artificial volume not present in the original three-dimensional subject.

Figure 2:
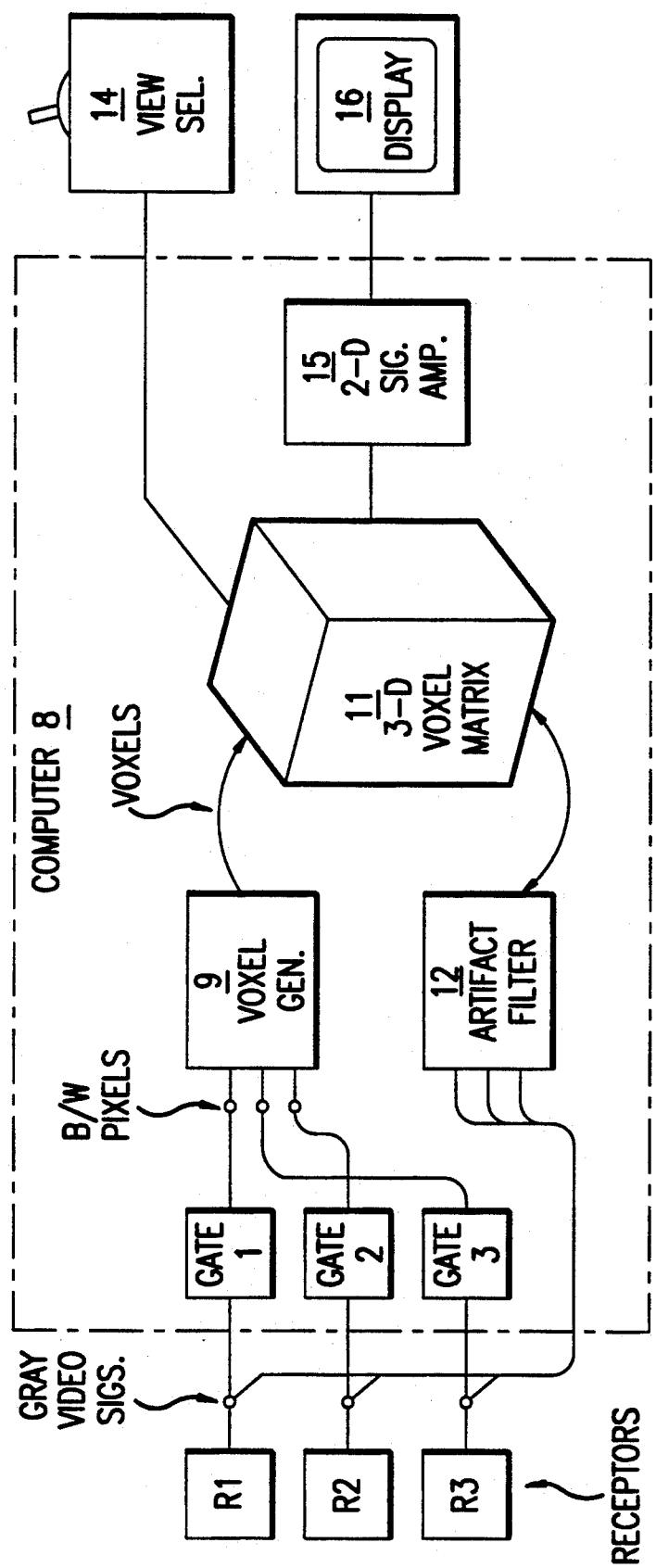
FIG. 2 is a schematic diagram of apparatus for processing the three-dimensional video signals.

FIG. 2 shows a computer system for carrying out the above described processing of three-dimensional video signals. The three receptors R1, R2, R3 convert the radiation from the subject S into three, two-dimensional gray scale video pixel signals applied respectively to three gates 1, 2 and 3. The gates have a threshold in the middle of the white-to-black or grey scale of pixel values, and pass only binary signals, that is black pixels above that threshold, and only white pixels below the threshold (B/W PIXELS), to the voxel generator 9 of a computer 8. When, as explained above with respect to FIG. 1, three black pixels, one from each two-dimensional video signal through a gate, coincide or intercept in time and three-dimensional space, a voxel is generated in a series of two-dimensional video voxel signals equivalent to a series of planes in three-dimensional space. These voxel series are stored by the computer 8 in the electrical equivalent of a three-dimensional storage matrix 11. The matrix is effectively scanned electrically by the computer under the control of a view selector 14 which can be adjusted to view the three-dimensional matrix at an angle along any selected axis, including angles other than the original radiation axes. Voxels around the selected view axis As are read out of the matrix 11 as pixels in a plane SV on the view axis to reconstruct a two-dimensional video signal representing a new view Is of the subject. This reconstructed video signal is then passed through a filter 12 which iteratively removes artifacts in a known manner to a display such as a cathode ray tube 16.

A suitable computer for carrying out the present invention is a Sun Work Station of Sun Microsystems, Inc., Sunnyville, Calif. A suitable algorithm adaptable to that computer is described by Mehrdad Soumekh in ICASSP 88, M Vol. II, Apr. 11–14 1988, pages 1280 to 1283.

Referring to FIG. 1, it can be seen that the three planar images Ix, Iy and Iz have volumes Bx, By and Bz which overlap in three dimensions, and are consistent with the existence of an artificial volume Va shown in phantom and not present in the real subject S. In the infrequent occurence of such overlaps, to prevent the possibility of such an artifact Va being stored in the voxel matrix 11 the voxel image in the matrix is compared by an artifact filter 12 with the three gray scale signals produced by the three radiation receptors R1, R2 and R3. A suitable artifact filtering algorithm is described in the previously mentioned Mehrdad Soumekh paper in ICASSP 88. If the artifact is not real, the corresponding gray signal will be of low intensity, and by an iterative process the filter, which is part of the computer 8, will exclude reproduction of the phantom volume Va in the voxel matrix.

Figure 3:
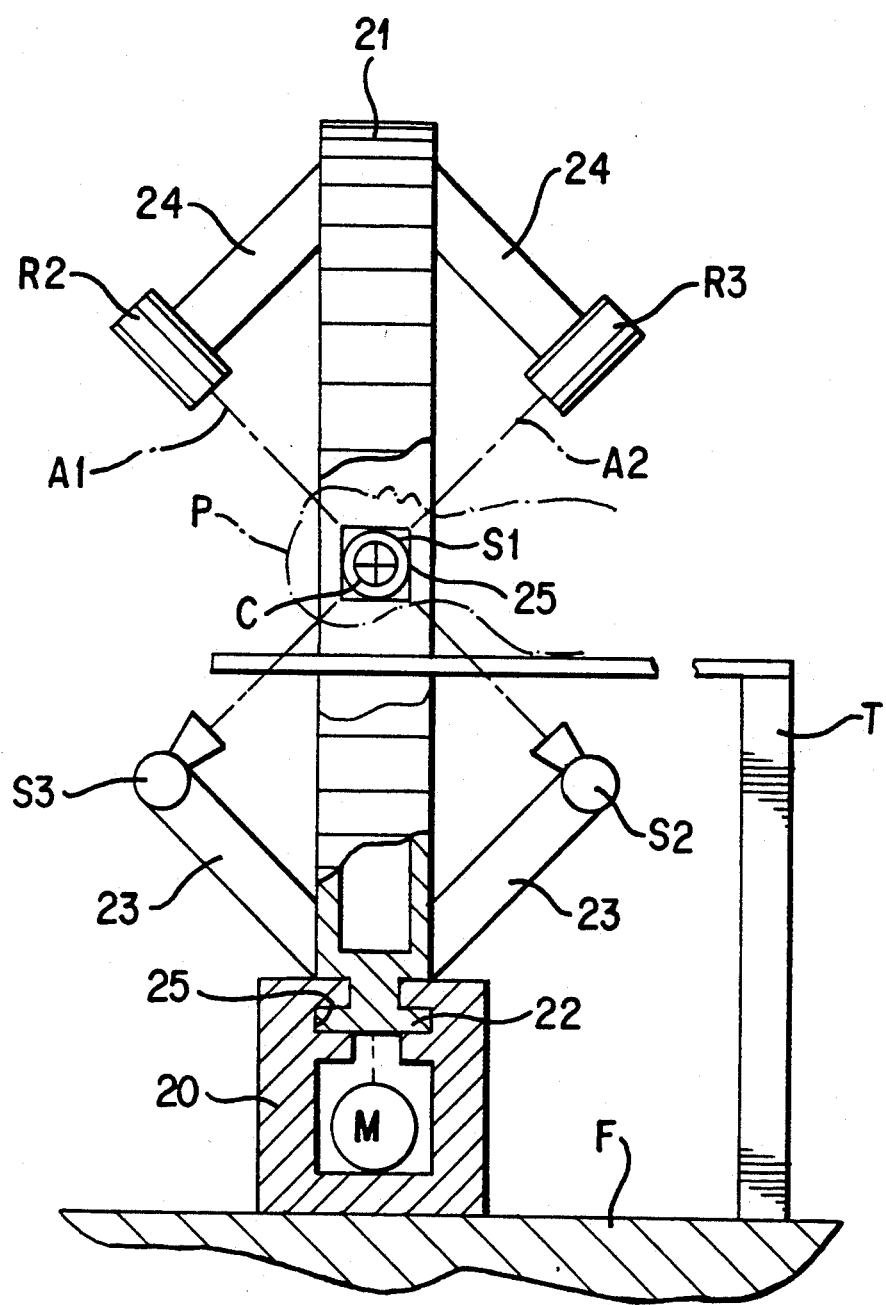
FIG. 3 is a side elevation of X-ray apparatus for exposing a subject.

In FIG. 3 is shown X-ray apparatus for carrying out the radiation step of the invention comprising a base 20 secured to a floor F for supporting a ring or wheel 21 having a peripheral, circular rail 22 sliding in a track 25 in the base. A motor M in the base engages the rail 22 rotating the ring about an isocenter C. A table T supports a patient P at the isocenter. 180 degrees apart on the ring are two sets of arms 23 and 24 respectively carrying X-ray tubes S2 and S3 and image intensifiers R2 and R3. On similar arms 25 extending radially in from the ring 90 degrees from the arms 23 and 24 are a third set of tube S1 and image intensifier (not shown). The sets of tubes and intensifiers are on radiation axes A1 and A2 intersecting the isocenter C through which the radiation axis of the third set of tube S1 and intensifier are aligned. The ring assembly allows all three sets of tubes and image intensifiers to be rotated to a fixed position with the three radiation sets aligned orthogonally with the patient at the isocenter. The patient may then be exposed with radiation on all three axes substantially simultaneously, subject only to the limitations of power supply to the three X-ray tubes. Processing of the three sets of video signals derived from the three images intensifiers to CRT display is then possible within a few seconds. Allowance must be made in scanning the three-dimensional X-ray record in the matrix for the fact that X-radiation is directed in a divergent cone as compared to the substantially parallel rays of light falling on a subject.

It should be understood that the present disclosure is for the purpose of illustration only, and that the invention includes all modifications and equivalents falling within the appended claims.

I claim:

1. A method of processing three-dimensional video signals representing a solid subject comprising:
   radiating the subject;
   receiving radiation from the subject on three axes intersecting the subject using radiation receptors to produce three planar images of the subject volume normal to the three respective radiation axes;
   converting the picture elements of the three planar images into three corresponding sets of planar video pixel signals;
   writing the three planar signal sets at the three radiation axes into superimposition in a three dimensional storage matrix such that coincidence of three pixels in the three respective images stores a single voxel representative of the superposition of the three pixels;
   addressing voxels on a selected view angle toward the three dimensional matrix other than the angles of the three radiation axes;
   reading, the addressed voxels of the selected view angle out of the matrix; and
   displaying or recording a two-dimensional image of the voxels read out at the selected view angle.

2. The method according to claim 1 wherein the three planar images are produced as gray scale signals.

3. The method according to claim 1 wherein the three planar images are converted into binary pixel signals before writing into the matrix.

4. The method according to claim 2 wherein the gray scale signals above and below a fixed threshhold are converted to black and white binary signals.

5. A method according to claim 1 wherein the radiation is light.

6. A method according to claim 1 wherein the planar images produced substantially simultaneously.

7. A method according to claim 1 wherein the three radiation axes are spaced substantial solid angles apart.

8. A method according to claim 1 wherein the three radiation axes are orthogonally spaced.

9. A method according to claim 1 wherein the three radiation axes are spaced apart by solid angles between forty-five and ninety degrees.

10. A method according to claim 1 wherein a voxel is generated by the addition of three pixels intercepting at the same address in three-dimensional space.

11. A method according to claim 10 wherein voxels having value less than the sum of three pixel values are filtered before being read out for display.

12. The method according to claim 1 wherein the three planar images are on a gray scale, and are iteratively compared with corresponding voxels in the matrix so as to exclude storage in the matrix of an artificial volume not present in the subject.

13. A method according to claim 1 wherein the display of the selected two-dimensional image is substantially simultaneous with the radiation of the subject.

14. A method according to claim 1 wherein the two-dimensional image read out of the matrix is displayed photographically.

15. Electrical apparatus for processing three dimensional video signals representing a solid subject comprising:
   three receptors of radiation on three different image axes intersecting the subject at three different angles for converting the radiation to three corresponding two-dimensional video images respectively represented by three sets of pixels;
   a voxel generator coupled to the three receptors for producing one three-dimensional set of voxels at the three-dimensional intercept of pixels projected from the three two-dimensional pixel sets;
   a three-dimensional voxel matrix for storing the voxels;
   adjustable means connected to the voxel matrix for selecting a viewing axis scanning the three-dimensional matrix at an angle other than the radiation axis angles, and addressing and reading out voxels within the selected view; and
   means coupled to the matrix for displaying the addressed and read out voxels of the selected three-dimensional view in a single two-dimensional image.

16. Apparatus according to claim 15 wherein the receptors are video cameras.

17. Apparatus according to claim 15 including means coupling respective radiation receptors to the voxel matrix comprising a modulator converting all pixel values above and below a threshold value to equal black and white values.

18. Apparatus according to claim 15 including a filter coupling the matrix to the displaying means for iteratively enhancing the voxel image read out of the matrix 19. Apparatus according to claim 15 wherein the displaying means is a cathode ray tube.

20. Electrical apparatus for angiographic examination of a subject comprising:
   three sets of X-radiation sources and receptors for directing beams along three separate radiation axes intersecting a volume within the subject and forming three two-dimensional images of the volume;
   electro-optical means producing three two-dimensional sets of video signal pixels from the three images;
   a voxel generator coupled to the three receptors for producing one three-dimensional set of voxels corresponding to the three-dimensional intercept of pixels projected frown the three two-dimensional pixels sets;
   a three-dimensional matrix for storing the voxels electrically;
   adjustable control means connected to the matrix for selecting a view axis for scanning the three-dimensional matrix at an angle other than the radiation axis angles, and addressing and reading out voxels with in the selected view; and
   means coupled to the matrix for displaying the addressed and read out voxels of the selected three-dimensional view in a single two-dimensional image.

21. Apparatus according to claim 20 wherein the matrix has an address with three dimensional coordinates for each voxel.

22. Apparatus according to claim 20 wherein the matrix has three dimensional addresses correponding electrically to the three dimensionally spaced elements of a geometric solid.

23. Apparatus according to claim 20 wherein the adjustable means comprises a controller selectively addressing voxels on intercepts around the selected view axis.

24. Apparatus according to claim 20 wherein the radiation receptors are X-ray image intensifiers.

25. Apparatus according to claim 20 including a modulator coupled between each radiation receptor and the voxel generator passing only pixels above a substantial threshold value.

* * * * *